US008071940B2

(12) United States Patent
Gómez Moreno et al.

(10) Patent No.: US 8,071,940 B2
(45) Date of Patent: Dec. 6, 2011

(54) SYSTEM TO REDUCE THE PRESSURE DROP IN A DIFFERENTIAL MOBILITY ANALYZER

(75) Inventors: Francisco Javier Gómez Moreno, Madrid (ES); Pablo Martínez Lozano Sinues, Madrid (ES); Manuel Martín Espigares, Madrid (ES)

(73) Assignee: Centro de Investigaciones Energeticas, Medioambientales Y Tecnologicas, Madrid (ES)

( * ) Notice: Subject to any disclaimer, the term of this patent is extended or adjusted under 35 U.S.C. 154(b) by 188 days.

(21) Appl. No.: 12/540,877

(22) Filed: Aug. 13, 2009

(65) Prior Publication Data

US 2011/0036979 A1   Feb. 17, 2011

(51) Int. Cl.
*H01J 49/06* (2006.01)
*G01N 1/22* (2006.01)

(52) U.S. Cl. ........................ 250/287; 250/282

(58) Field of Classification Search ........... 250/281–300
See application file for complete search history.

(56) References Cited

U.S. PATENT DOCUMENTS

| | | | |
|---|---|---|---|
| 6,230,572 B1 * | 5/2001 | Pui et al. | 73/863.21 |
| 6,787,763 B2 * | 9/2004 | De La Mora et al. | 250/287 |
| 7,161,143 B2 * | 1/2007 | De La Mora et al. | 250/287 |
| 7,261,007 B2 * | 8/2007 | Haglund et al. | 73/863.21 |
| 7,626,161 B2 * | 12/2009 | Labowsky et al. | 250/287 |
| 2003/0116708 A1 * | 6/2003 | De la Mora et al. | 250/288 |
| 2006/0266132 A1 * | 11/2006 | Cheng et al. | 73/865.5 |
| 2008/0149824 A1 * | 6/2008 | Miller et al. | 250/287 |
| 2009/0173670 A1 * | 7/2009 | Okuda et al. | 209/127.1 |
| 2010/0213366 A1 * | 8/2010 | Fernandez De La Mora et al. | 250/282 |

FOREIGN PATENT DOCUMENTS

| WO | 9941585 A2 | 8/1999 |
|---|---|---|
| WO | 2007072942 A1 | 6/2007 |

OTHER PUBLICATIONS

Chen et al., Design and Evaluation of a Nanometer Aerosol Differential Mobility Analyzer (Nano-DMA), J. Aerosol Sci. vol. 29, No. 5/6, pp. 497-509, 1998.*
Martinez-Lozano, P. and Fernandez de la Mora, J. 2006. "Resolution improvements of a nano-DMA operating transonically." Journal of Aerosol Science. 37, 500-512.*
Rosser, S. et al., Vienna-Type DMA of High Resolution and High Flow Rate, Aerosol Science and Technology, 2005, 39:1191-1200.

* cited by examiner

*Primary Examiner* — Jack Berman
*Assistant Examiner* — Wyatt Stoffa
(74) *Attorney, Agent, or Firm* — Andrew D. Gerschutz; Tristan A. Fuierer; Moore & Van Allen, PLLC

(57) ABSTRACT

System to reduce the pressure drop in a Vienna-type differential mobility analyzer (DMA). It is built to favor the flow axilsymmetry, with no restrictions to avoid strong pressure drops and high pumping capacities. It comprises an electrical isolator, a metallic cone to stabilize the flow, all in one instrument covering a size range of 1 to 600 nm. The electrical isolator is capable of a potential difference of up to 14 kV. It can be used to measure ions and particles in the size range already mentioned with resolutions up to 12.

8 Claims, 3 Drawing Sheets

SYSTEM TO REDUCE THE PRESSURE DROP IN A DIFFERENTIAL MOBILITY ANALYZER

TECHNICAL FIELD OF THE INVENTION

The present invention refers to a device able to measure ions and particles from 1 nm up to 600 nm, with resolution of up to 12. This is achieved by decreasing the pressure drop in Vienna-type Differential Mobility Analyzers (DMAs) (Winklmayr et al., 1991). Such size range is reached with a moderate pumping capacity, such as a vacuum pump. At the same time, the device allows up to a 14-kV potential difference, and thus is able to measure particles of several hundred nanometers.

BACKGROUND OF THE INVENTION

DMAs (Differential Mobility Analyzers) classify charged particles based on their capacity to migrate in an electric field. A DMA basically works by introducing a charged particle sample in a clean gas flow, which drags them through a region where there is an electrical field. The combination of the electrical and the flow fields classify the particles as a function of their electrical mobility. At the same time, this is a function of the particle size and charge. Knowing the particle charge distribution, it is possible to determine the particle size distribution.

DMAs have been traditionally used in measuring the particle size distributions in environmental applications such as atmospheric aerosols and combustion emissions. The traditional size range has been 15-1000 nm. Modern nanotechnology and other analytical applications require extending this range down to 1 nm with high resolution, high enough to classify very close particle sizes. Some nanomaterial properties drastically depend on the particle size used during the material synthesis, e.g., the particles must be highly monodisperse (having the same size). This can only be reached with high resolution instrumentation. So, the DMA characteristics are defined not only by the particle size range, but also by the resolution reached in that range (Rosser and Fernández de la Mora, 2005).

In the case of non diffusive particles, the ideal instrument resolution comes from the ratio between the sheath flow rate and the aerosol flow rate (Knutson and Whitby, 1975). However, the limiting factor to reach high resolution in the nanometric range is Brownian diffusion. A possible strategy to minimize the diffusive effect is to increase the Peclet number, therefore, increasing the Reynolds number for a selected particle size (de Juan et al., 1998). However, at the same time the flow must be kept under a laminar regime. In case of appearance of turbulence, the instrument resolution would be drastically degraded.

An additional condition is that the gas flow must be axilsymmetric. In the original Winklmayr design, the sheath flow rate is radially extracted. To keep the flow axilsymmetry it is necessary to have a constriction downstream of the aerosol outlet slit. This means a high pressure drop, which preempts high flow rates and high resolutions. An attempt to solve this problem was that of Rosser and Fernández de la Mora (2005) and the Martinez Lozano et al. (2004) previous prototype, where there were two outlet chambers to avoid the asymmetry caused by the conventional outlets in DMAs. When duplicating the chambers, it is necessary to include a similar constriction to the traditional ones, increasing the pressure drop in the sheath flow outlet. All these problems have forced the use two different DMAs to cover the 1-600 nm size range, because one instrument was not able to cover it with enough and adequate resolution.

In the proposed system, the present invention, the sheath flow outlet is produced with no constriction in the chamber. At the same time, the sheath flow outlet is completely axial and allows to have relatively low pressure drop and to reach high Reynolds numbers. This pressure drop is minimized by not using diffusers and with parallel walls, without divergent angles. All of this produces an instrument able to measure in the range 1 to 600 nm, with resolutions higher than 10 and keeping the aerosol inlet and outlet slit distances as in the Winklmayr DMA. Further, the sheath gas extraction system is very easy to machine and assemble.

BRIEF DESCRIPTION OF THE INVENTION

The problems mentioned above are solved by a device (sheath gas extraction system) to reduce the pressure drop in a Vienna type differential mobility analyzer (DMA) providing an axilsymmetry flow according to independent claim 1.

The device of the invention (sheath gas extraction system) comprises a first isolating piece arranged to allow the sheath gas to be extracted in an axial direction, a second stabilizing piece adapted to stabilize the flow, and a third extraction piece adapted to extract the sheath flow, wherein the third extraction piece is connected to the pumping system.

The DMA comprises a high efficiency filter, which allows the sheath flow to be particle free and uniformly distributed. After going through a laminarization screen and a convergent section, the sheath flow rate goes through the particle classification section. Downstream, the gas is extracted in the axial direction after going through a first Teflon drilled piece. This piece allows the sheath gas extraction system to have a single outlet chamber and it is at the same time the inner electrode support and an electrical isolator, adapted to fit in the DMA inner electrode piece. Downstream, the gas is finally extracted by a second Teflon convergent piece and a third metallic cone shape piece. The objective of this last piece is to avoid flow instabilities which could be propagated upstream thus deteriorating the resolution.

The sheath flow outlet system comprising these three pieces permits the attainment of resolutions of up to 12 measuring ~1 nm ions and a maximum potential difference of 14 kV. This last value, together with the inlet/outlet slit distance, allows to measure particles up to 600 nm with a sheath/aerosol flow rate ratio of 3/0.3 and a theoretical resolution of 10.

The sheath gas extraction system is mounted to the DMA analyzer. The first isolating piece is in contact with the inner electrode support piece. The third extracting piece is connected to the first piece and allows the extraction of the sheath flow and is connected to the pumping system.

As a consequence, the outlet flow is characterized by an axilsymmetry flow and with no restriction to this flow producing a low pressure drop and this allows the attainment of high flow rates using a moderate pumping capacity.

The sheath gas extraction system to reduce the pressure drop in a differential mobility analyzer (DMA) is able to cover the 1-600 nm range, reaching resolutions around 12 for the smallest size and working at high flow rates.

BRIEF DESCRIPTION OF THE DRAWINGS

To complete the previous description and with the objective of having a better understanding of the invention, some representative figures are included. This set is merely indicative and not limitative and includes:

FIGS. 3-6 showing different pieces the system:

FIG. 3 showing the cone located downstream designed to stabilize the flow after the piece 3 (FIG. 6).

FIG. 5 corresponding with piece 1, which connects with the extraction pump and allow the axial extraction.

FIG. 6 showing a sectional view of the electrical isolator.

DETAILED DESCRIPTION OF THE PREFERRED EMBODIMENT

Figure 6:
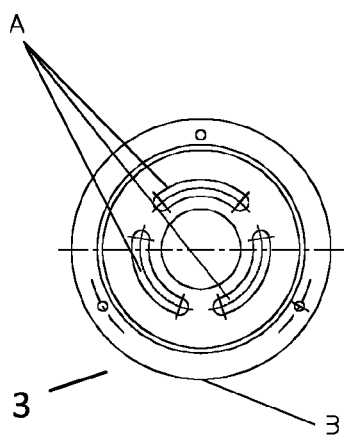

The sheath gas extraction system (FIG. 2) is formed by a circular Teflon piece (3), with three concentric slots (A) showed in FIG. 6. The sheath gas goes axially through these slots (A). There is a fourth orifice, radially machined where the monodisperse gas outlet tube is inserted (B). This tube is screwed to the metallic conic piece (2), located downstream the piece (3). At the same time, the inner electrode support (4) is screwed to the conic piece (2), resting the Teflon piece (3) between the conic piece (2) and the inner electrode support (4). After assembling, these pieces (FIG. 2) are supported in the outer electrode (6 in FIG. 1). Finally, the Teflon piece (1) is screwed to the set.

Figure 3:
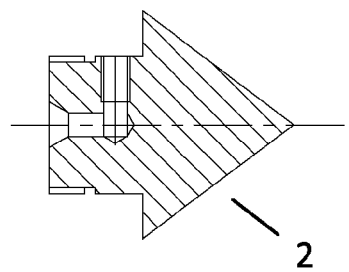
Figure 4A:
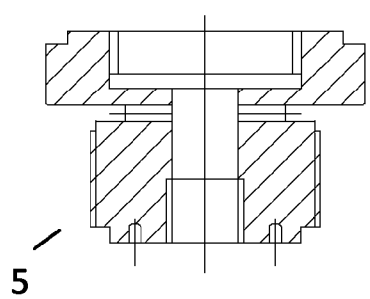
FIGS. 4a and 4b showing a lateral and sectional view of the piece located upstream of piece 3 (FIG. 6), through which the monodisperse aerosol is extracted.
Figure 4B:
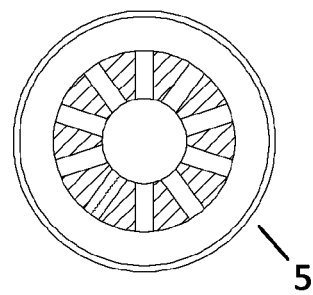
Figure 5:
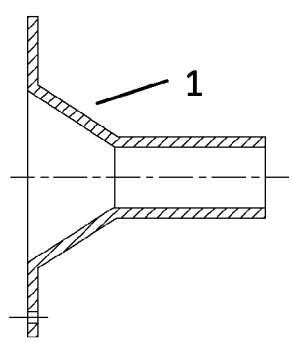

FIGS. 3-5 show different pieces the system: In FIG. 3 it is shown the cone located downstream designed to stabilize the flow after the piece (3) (FIG. 6). In FIGS. 4a and 4b there are shown a lateral and sectional view of the piece located upstream of piece 3 (FIG. 6), through which the monodisperse aerosol is extracted. Finally FIG. 5 corresponds with piece 1, which connects with the extraction pump and allows the axial extraction.

Figure 1:
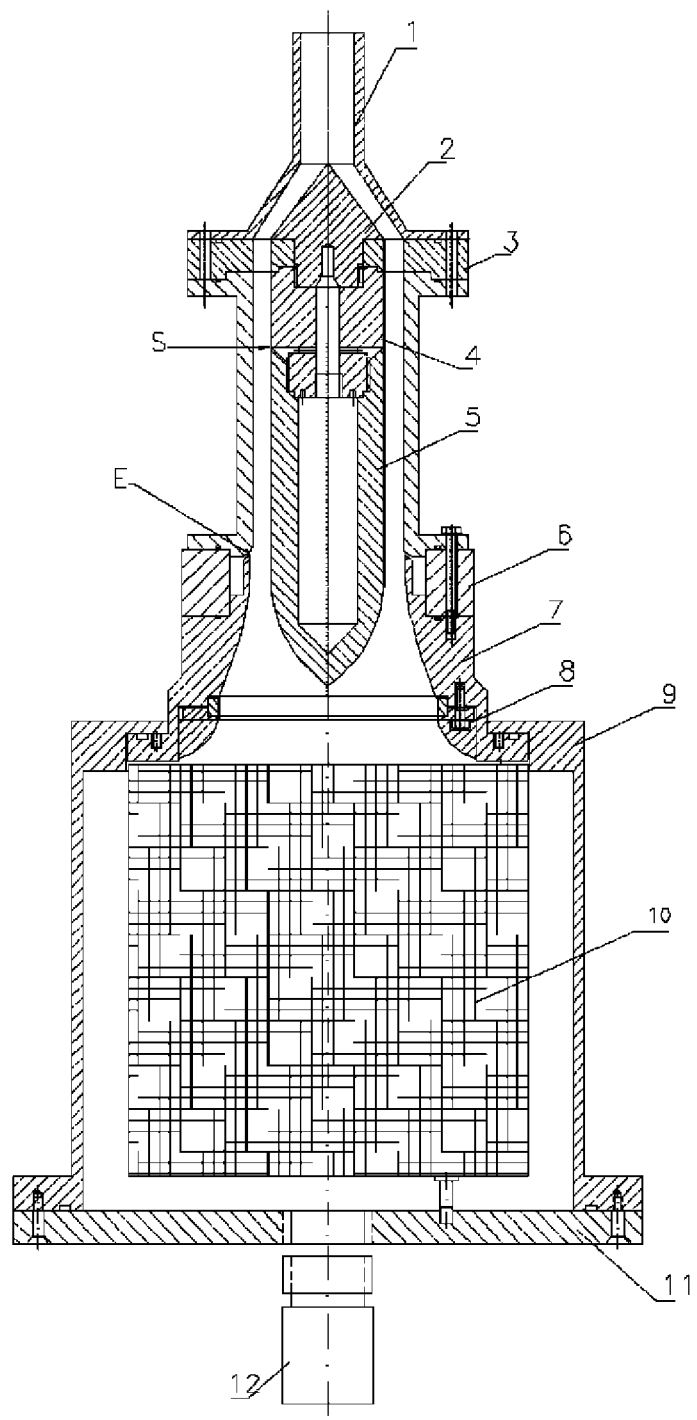
FIG. 1 showing a lateral view of the complete DMA.
Figure 2:
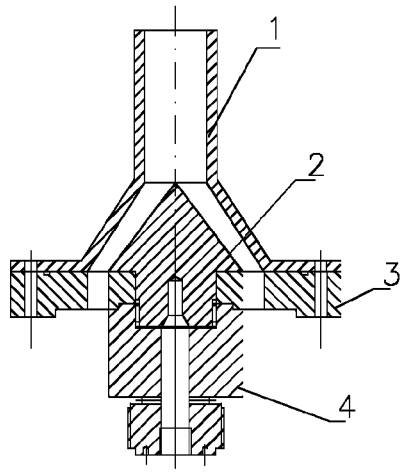
FIG. 2 showing a detailed lateral view of the sheath flow extraction system, it is possible to see there is one chamber and there are no constrictions.

The complete DMA assemble is shown in FIG. 1. The sheath gas enters by the inlet tube (12) arriving to the chamber formed by pieces (9) and (11). The gas radially enters through an HEPA filter (10) and a laminarization screen tightened by piece (8). It is accelerated in the convergent section (7) and is mixed with the polydisperse aerosol in the position (E) of FIG. 1. Particles are classified (at 5 and 6) in function of their mobility and only those within a narrow mobility range are extracted through the slit (S) in FIG. 1. The sheath gas goes downstream through the piece (3) and is finally extracted through the piece (1).

Figure 7:
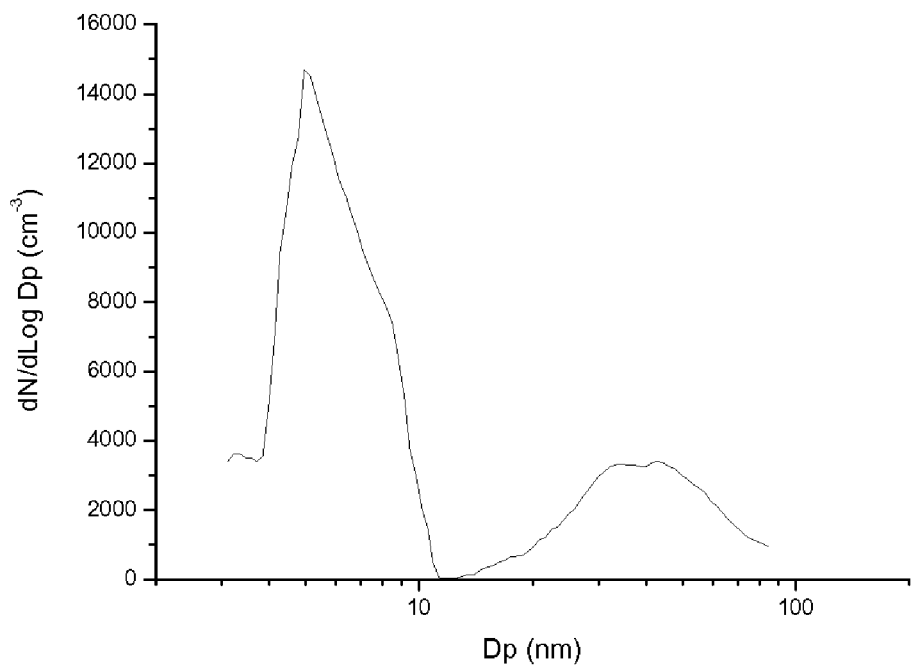
FIG. 7 corresponding with an atmospheric aerosol size distribution measured with this instrument.

This instrument can be used in the aerosol technology field to measure polydisperse particle size distributions (i.e. atmospheric or combustion aerosols). To illustrate this, FIG. 7 shows an atmospheric aerosol size distribution obtained by the instrument described here. Two peaks are observed: a nanometer one and a submicrometric one. Until the present invention it was necessary to use two different DMAs, with different size ranges, to measure simultaneously both maxima.

Figure 8:
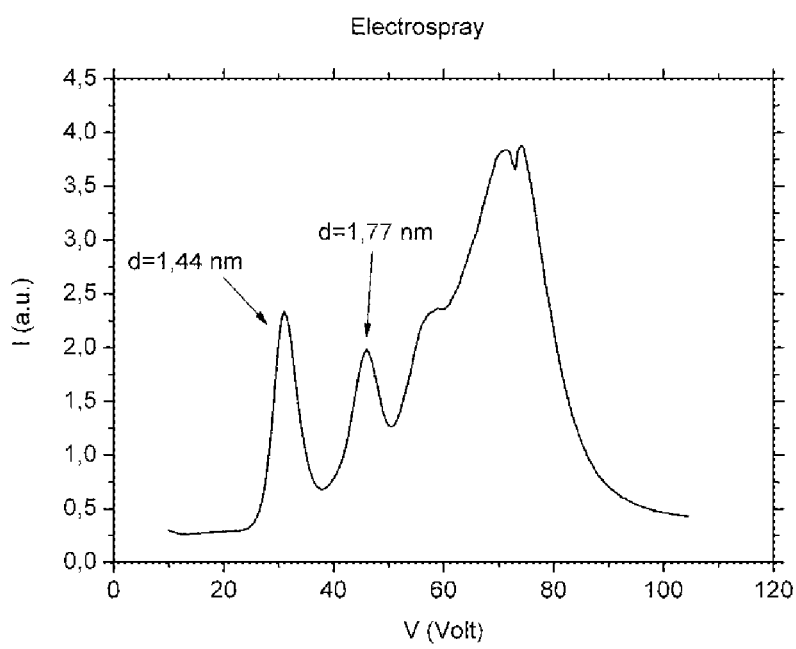
FIG. 8 showing an ion mobility spectrum measured with this instrument.

At the same time, it can be used to generate monodisperse particles. This technique is used to synthesize nanomaterials. Its resolution allows the classification of particles with similar sizes from a complex mixture. FIG. 8 shows an ion mobility spectrum and how the instrument is able to separate 1.44 and 1.77 nm ions.

In a preferred embodiment the sheath gas extraction system is shaped with any combination of the following having the dimensions and materials listed below. Preferably, the slots (A) of piece (3) are shaped with an inner radius of substantially 50 mm, an outer radius of substantially 66 mm, being the arc angle of substantially 95 degrees.

Preferably, the second stabilizing piece (2) is cone shaped with a height of substantially 33 mm and the aperture of the cone is substantially 37 degrees.

Preferably, the piece (1) is shaped with an orifice with an inner radius of substantially 66 mm and an orifice of outer radius of substantially 24 mm.

Preferably, the inert material allows a 14 kV potential difference. Advantageously, the inert material is PTFE (Teflon).

Preferably, the conductive material is stainless steel.

In a more preferred embodiment, the sheath gas extraction system has all of the dimensions listed above, the inert material is PTFE and the conductive material is stainless steel.

REFERENCES de Juan, L. and Fernandez de la Mora, J. (1998). Size Analysis of Nanoparticles and Ions: Running a Vienna DMA of Near Optimal Length at Reynolds Numbers up to 5000. J. Aerosol Science 29:617-626.

Knutson, E., 0 and Whitby, K. T. (1975). Aerosol classification by electric mobility: apparatus, theory and applications. J. Aerosol Sci. 6:443-451.

Martinez-Lozano, P et al. Generation of Highly Monodisperse Particles via Electrical Mobility Analysis. Trends in Nanotechnology Conference (TNT2004), Segovia, 13-17 Sep. 2004.

Rosser, S. and Fernández de la Mora, J. Vienna-Type DMA of High Resolution and High Flow Rate. Aerosol Science and Technology, 2005, 39, 1191-1200.

Winklmayr, W., Reischl, G. P., Lindner, A. O. and Berner, A., (1991). A New Electromobility Spectrometer for the Measurement of Aerosol Size Distributions in the Size Range From 1 to 1000 nm, J. Aerosol Sci. 22:289-296.

We claim:

1. A sheath gas extraction system adapted to be engaged to a Vienna type differential mobility analyzer (DMA) to reduce the pressure drop in the DMA while providing an axisymmetric flow, the DMA comprising a first portion comprising an inner electrode support and a second portion comprising a particle classification section outlet, the sheath gas extraction system comprising: a first isolating piece (3) made from a substantially insulating and chemically inert material, wherein the first isolating piece (3) is substantially axisymmetric and comprises at least two slots (A) substantially around a revolution axis; a second stabilizing piece (2) made from a conductive material, wherein the second stabilizing piece (2) is substantially conic and comprises a substantially circular orifice along the revolution axis; and a third extraction piece (1) made from a substantially insulating and chemically inert material, wherein the third extraction piece (1) is substantially convergent in a downstream direction and tubular, the sheath gas extraction system being arranged in a downstream configuration wherein: the first isolating piece (3) is adapted to engage with the first portion of the DMA at the particle classification section outlet and with the second stabilizing piece (2); the second stabilizing piece (2) is adapted to engage with the first isolating piece (3); and the third extraction piece (1) is adapted to engage with the first isolating piece (3).

2. The system according to claim 1 wherein the slots (A) of the first isolating piece (3) are shaped with an inner radius of substantially 50 mm, an outer radius of substantially 66 mm, and an arc angle of substantially 95 degrees.

3. The system according to claim 1 wherein the second stabilizing piece (2) is cone shaped with a height of substantially 33 mm, the aperture of the cone being substantially 37 degrees.

4. The system according to claim 1 wherein the third extraction piece (1) is shaped with an orifice of inner radius of substantially 66 mm, and an orifice of outer radius of substantially 24 mm.

5. The system according to claim 1 wherein the inert material of the first isolating piece (3) and/or the third extraction piece (1) allows a 14 kV potential difference.

6. The system according to claim 1 wherein the inert material of the first isolating piece (3) and/or the third extraction piece (1) is PTFE (Teflon).

7. The system according to claim 1 wherein the conductive material is stainless steel.

8. A differential mobility analyzer comprising a sheath gas extraction system according to claim 1 engaged thereto.

* * * * *